United States Patent
Mazurek (10) Patent No.: US 9,089,196 B2
(45) Date of Patent: Jul. 28, 2015

(54) SKINCARE PAD-BASED APPLICATION SYSTEM AND METHOD

(71) Applicant: Robert Mazurek, Scottsdale, AZ (US)

(72) Inventor: Robert Mazurek, Scottsdale, AZ (US)

(*) Notice: Subject to any disclaimer, the term of this patent is extended or adjusted under 35 U.S.C. 154(b) by 0 days.

(21) Appl. No.: 14/165,287

(22) Filed: Jan. 27, 2014

(65) Prior Publication Data

US 2014/0209118 A1     Jul. 31, 2014

Related U.S. Application Data (60) Provisional application No. 61/757,018, filed on Jan. 25, 2013.

(51) Int. Cl.
| | |
|---|---|
| B65D 69/00 | (2006.01) |
| B65D 71/00 | (2006.01) |
| A45D 40/24 | (2006.01) |
| A45D 34/04 | (2006.01) |

(52) U.S. Cl.
CPC ........ *A45D 34/04* (2013.01); *A45D 2200/1036* (2013.01); *A45D 2200/25* (2013.01)

(58) Field of Classification Search
CPC ... A45D 40/00; A45D 40/24; A45D 40/0087; A45D 34/04; A45D 2200/25; A45D 2200/10; A45D 2200/1009; A45D 2200/1018; A45D 2200/1027; A45D 2200/1054; A45D 2200/1036; A45D 2200/1063; A45C 11/008; A61F 15/001; A61K 8/0208; A61K 8/0212; B65D 83/0445; B65D 83/08; B65D 83/0805; B65D 83/2853; B65D 83/0894; B65D 2575/28; B65D 2575/30
USPC ......... 132/317, 200, 294, 286, 319, 320, 333; 401/6, 7, 18, 19, 25, 27, 34, 130, 266; 510/130, 137, 138, 140; 221/103, 15, 221/34; 424/401, 443; 604/3; 206/581, 823, 206/229, 38, 235, 389, 397, 534, 534.1, 206/535, 484, 441, 812, 820, 824, 440; 15/107, 118, 208, 209.1, 210.1, 227, 15/229.14, 244.4; 53/473, 474
See application file for complete search history.

(56) References Cited

U.S. PATENT DOCUMENTS

| | | | | |
|---|---|---|---|---|
| 1,888,314 | A | * | 11/1932 | Framke .................... 132/317 |
| 2,175,133 | A | * | 10/1939 | Singleton ................. 132/317 |
| 2,561,400 | A | * | 7/1951 | Morrell ..................... 132/314 |
| 2,621,784 | A | * | 12/1952 | Van Boytham ........... 206/361 |
| 2,637,439 | A | * | 5/1953 | Banks ....................... 206/581 |
| 3,608,566 | A | * | 9/1971 | Storandt ................... 132/312 |
| 3,608,708 | A | * | 9/1971 | Storandt ................... 206/361 |
| 3,635,567 | A | * | 1/1972 | Richardson, Jr. ........ 401/132 |

(Continued)

OTHER PUBLICATIONS http://karunaskin.com/products/skin-transformation-kit.html (2009-2013).*

(Continued)

*Primary Examiner* — Vanitha Elgart
(74) *Attorney, Agent, or Firm* — Adam D. Stevens; Kirton McConkie (57) ABSTRACT

A skincare pad-based application system and method utilizes a container containing individually packaged skincare products contained on disposable pads and arranged in a time-based order of intended use. The physical arrangement of the various products in the container or other packaging material simplifies application and increases the likelihood that products will be applied correctly and for maximum effect.

10 Claims, 5 Drawing Sheets

(56) References Cited

U.S. PATENT DOCUMENTS

| | | | | |
|---|---|---|---|---|
| 3,903,345 | A * | 9/1975 | Baker et al. | 442/395 |
| 4,218,155 | A * | 8/1980 | Weidner | 401/132 |
| 4,860,899 | A * | 8/1989 | McKee | 206/534 |
| 5,242,057 | A * | 9/1993 | Cook et al. | 206/581 |
| 5,320,217 | A * | 6/1994 | Lenarz | 206/209 |
| 5,337,897 | A * | 8/1994 | Yablans | 206/581 |
| 5,368,581 | A * | 11/1994 | Smith et al. | 604/290 |
| 5,562,642 | A * | 10/1996 | Smith et al. | 604/289 |
| 5,857,564 | A * | 1/1999 | Hymowitz | 206/209 |
| 6,159,487 | A * | 12/2000 | Znaiden et al. | 424/402 |
| 6,168,028 | B1 * | 1/2001 | Telesca et al. | 206/776 |
| 6,294,182 | B1 * | 9/2001 | Znaiden et al. | 424/402 |
| 6,358,516 | B1 | 3/2002 | Harod | |
| 6,581,775 | B1 * | 6/2003 | Hagopian | 206/572 |
| 6,708,826 | B1 * | 3/2004 | Ginsberg et al. | 206/535 |
| 6,820,744 | B2 | 11/2004 | Hoffman | |
| 7,264,119 | B2 * | 9/2007 | Navickas | 206/390 |
| 7,316,310 | B2 * | 1/2008 | Saschin | 206/232 |
| 7,806,877 | B2 * | 10/2010 | Kang et al. | 604/306 |
| 7,866,476 | B2 * | 1/2011 | McGonagle et al. | 206/535 |
| 8,496,108 | B2 * | 7/2013 | Bahcall | 206/210 |
| 2002/0104775 | A1 * | 8/2002 | Hoffman | 206/581 |
| 2002/0150610 | A1 * | 10/2002 | Kono et al. | 424/443 |
| 2004/0168951 | A1 * | 9/2004 | Mackie, Jr. | 206/534 |
| 2004/0191330 | A1 * | 9/2004 | Keefe et al. | 424/638 |
| 2005/0074483 | A1 * | 4/2005 | Lange | 424/443 |
| 2005/0167315 | A1 * | 8/2005 | Krey | 206/494 |
| 2006/0022060 | A1 | 2/2006 | Forte-Pathroff | |
| 2006/0065670 | A1 * | 3/2006 | Doublet et al. | 221/1 |
| 2007/0017840 | A1 * | 1/2007 | Louis Dit Picard et al. | 206/440 |
| 2007/0062843 | A1 * | 3/2007 | Rudd | 206/581 |
| 2007/0243155 | A1 * | 10/2007 | Bottiglieri et al. | 424/70.23 |
| 2008/0023025 | A1 * | 1/2008 | Burtzlaff et al. | 132/320 |
| 2008/0128311 | A1 * | 6/2008 | Ford | 206/534 |
| 2008/0241200 | A1 | 10/2008 | Sojka | |
| 2008/0264824 | A1 * | 10/2008 | Alejandra | 206/581 |
| 2009/0038100 | A1 * | 2/2009 | Larsen et al. | 15/229.11 |
| 2009/0050172 | A1 * | 2/2009 | Christ | 132/320 |
| 2009/0156451 | A1 | 6/2009 | Seidling | |
| 2009/0255843 | A1 * | 10/2009 | Krakowski | 206/534 |
| 2009/0261014 | A1 * | 10/2009 | Reape et al. | 206/531 |
| 2010/0285080 | A1 * | 11/2010 | Scimeca et al. | 424/401 |
| 2010/0331412 | A1 * | 12/2010 | Lawler Kenet et al. | 514/557 |
| 2011/0067718 | A1 * | 3/2011 | Lee | 132/200 |
| 2011/0308992 | A1 * | 12/2011 | Bahcall | 206/581 |
| 2013/0139841 | A1 * | 6/2013 | Dumousseaux et al. | 132/200 |
| 2013/0270150 | A1 * | 10/2013 | Bahcall | 206/581 |

OTHER PUBLICATIONS

Kate Somerville, "Get Gorgeous Kit (Nordstrom Exclusive)," http://shop.nordstrom.com/s/kate-somerville-get-gorgeous-kit-nordstrom-exclusive-157-value/3309422, (2014).

Somme Institute, "Somme Institute: 5-Step Skincare Regimen," http://www.youtube.com/watch?v=tUlfb39o1XY, (Nov. 21, 2008).

Somme Institute, "Somme Mobiel Travel Kit," http://www.sommeinstitute.com/productdetails.cfm? SKU=SO-9000MT, (2014).

HIP2SAVE, "Free MDT5 Skin-Care Sample Pack," http://hip2save.com/2010/12/26/free-mdt5-skin-care-sample-pack/, (Dec. 26, 2010).

Dr. Denese, "Dr. Denese's Six Step Skin Care Program," http://www.drdenese.com/denese-six-step-skin-care program, (2014).

Dr. Denese, "15 Day SkinScience Booster Program," http://www.drdenese.com/weekly-skin-care-treatments/skin-care-booster-program-30, (2014).

Clinique, "3-Step Skin Care," http://www.clinique.com/cms/product/3_step_grid.tmpl, (2014).

\* cited by examiner

SKINCARE PAD-BASED APPLICATION SYSTEM AND METHOD

CROSS-REFERENCE TO RELATED APPLICATIONS

This application claims the benefit of U.S. Provisional Application No. 61/757,018, filed Jan. 25, 2013.

BACKGROUND OF THE INVENTION

1. Field of the Invention

The present invention relates to skincare, and more particularly to a pad-based skincare application system and method.

2. Background and Related Art

Skincare products have increased in complexity of application and use. Many users of skincare products now worry about complicated skincare regimens involving the application of a variety of products. In many instances, the complexity of the correct application procedures and orders causes users to apply the products incorrectly, reducing the effectiveness of the skincare regimen.

In some instances, multiple different skincare products having different intended purposes are packaged in similar containers. Users of the products may apply such products incorrectly, including by using incorrect amounts of product or by mistakenly using one product when they intended to use another product. Even when a user recognizes that an incorrect product has been selected, product may be wasted before such recognition occurs. In short, there are a variety of unaddressed problems associated with current skincare products and regimens.

BRIEF SUMMARY OF THE INVENTION

A skincare pad-based application system and method is disclosed that utilizes a container or package containing individually packaged skincare products contained on disposable pads and arranged in a time-based order of intended use. The physical arrangement of the various products in the container or other packaging material simplifies application and increases the likelihood that products will be applied correctly and for maximum effect.

A skincare application system according to implementation of the invention may include a package and a plurality of individually sealed applicators for applying a plurality of differing skincare products within the package, wherein each of the applicators is pre-loaded with one of the plurality of skincare products. The plurality of applicators is arranged in the package in an order that corresponds to a time-based order in which the skincare products are intended to be applied, such that removing applicators from the package in the time-based order and applying the skincare product of each removed applicator in the order that it is removed ensures application of the plurality of skincare products in a proper order according to a time-based skincare regimen.

The time-based skincare regimen may be a repeating regimen that repeats once per a first time period. In such a regimen, the plurality of skincare products may include a first skincare product intended for application once at the start of a first time period and a second skincare product intended for periodic application one or more times between applications of the first skincare product. The first time period may be divisible into a plurality of intervals, such as days. The first skincare product may be intended for application at the start of the first interval, and the second skincare product may be intended for periodic application at the start of other of the plurality of intervals. The plurality of skincare products may include a third skincare product intended for application at the start of intervals not intended for application of either the first skincare product or the second skincare product.

In one example, the first time period is a week and the plurality of intervals are days. The first skincare product is intended for application on the first day of the week. The second and third skincare products are intended for alternating application on the second through seventh days of the week. A system and package may contain a multiple-week supply of applicators.

In one example of the skincare system, the first skincare product comprises a skincare composition comprising an effective amount of multiple alpha hydroxy acids, the second skincare product comprises a skincare composition comprising an effective amount of an antioxidant, and the third skincare product comprises a skincare composition comprising an effective amount of a retinoid.

The individually sealed applicators may be ordered in the package utilizing a variety of methods. In one example, the applicators are ordered by physical placement only, wherein each individually sealed applicator is not physically connected to any other sealed applicators, and wherein each individually sealed applicator is physically located more proximate or less proximate an opening of the package than any other individually sealed applicators. In a second example, the applicators are ordered by physical placement and connection to adjacent individually sealed applicators, wherein each individually sealed applicator is physically connected to any immediately adjacent sealed applicators, and wherein each individually sealed applicator is physically located more proximate or less proximate an opening of the package than any other individually sealed applicators. In a third example, the applicators are ordered by connection to adjacent individually sealed applicators only, wherein each individually sealed applicator is physically connected to any immediately adjacent sealed applicators as a ribbon of individually sealed applicators.

In various implementations of the system, each of the individually sealed applicators includes a removable seal covering the skincare product preloaded on the applicator. In implementations of the system, each of the applicators is or includes a pad configured to facilitate application of one of the skincare products. The pad may include a rear side having a sleeve configured to receive human fingers therein and a front side having an application surface preloaded at a portion thereof with one of the skincare products and a seal sealed to the application surface around the portion of the application surface preloaded with skincare product.

In further implementations of the invention, a skincare pad-based application system includes a package and a plurality of individually sealed pads for applying a plurality of differing skincare products within the package, wherein each of the pads is pre-loaded with one of the plurality of skincare products. The plurality of pads may be arranged in the package in an order that corresponds to a time-based order in which the skincare products are intended to be applied, such that removing pads from the package in the time-based order and applying the skincare product of each removed pad in the order that it is removed ensures application of the plurality of skincare products in a proper order according to a time-based skincare regimen. Such implementations may include features of the implementations discussed above wherein the "applicator" of such implementations is a pad.

Further implementations of the invention provide a method for producing a skincare applicator-based application system. The method includes providing a package, providing a plurality of individually sealed applicators for applying a plurality of differing skincare products, wherein each of the applicators is pre-loaded with one of the plurality of skincare products, and arranging the plurality of applicators in the package in an order that corresponds to a time-based order in which the skincare products are intended to be applied according to a time-based skincare regimen.

According to implementations of the method, the individually sealed applicators may be ordered in the package utilizing a variety of methods. In one example, the individually sealed applicators are ordered by physical placement only, wherein each individually sealed applicator is not physically connected to any other sealed applicators, and wherein each individually sealed applicator is physically located more proximate or less proximate an opening of the package than any other individually sealed applicators. In a second example, the individually sealed applicators are ordered by physical placement and connection to adjacent individually sealed applicators, wherein each individually sealed applicator is physically connected to any immediately adjacent sealed applicators, and wherein each individually sealed applicator is physically located more proximate or less proximate an opening of the package than any other individually sealed applicators. In a third example, the individually sealed applicators are ordered by connection to adjacent individually sealed applicators only, wherein each individually sealed applicator is physically connected to any immediately adjacent sealed applicators, as a ribbon of individually sealed applicators.

In some implementations of the method, each of the applicators includes or may be a pad configured to facilitate application of one of the skincare products. In some implementations, the applicator includes or is a pad, and providing a plurality of individually sealed applicators for applying a plurality of differing skincare products includes loading an application surface of the pad with one of the skincare products and providing a seal over the skincare product that is sealed to the application surface around the skincare product.

Implementations of the invention may vary from the specifics discussed in the summary of the invention, and the scope of the claimed invention is to be determined from the appended claims.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

A skincare application system and method is disclosed that utilizes a container or package containing individually packaged or sealed skincare products contained on disposable pads or other applicators and arranged in a time-based order of intended use. The physical arrangement of the various products in the container or other packaging material simplifies application and increases the likelihood that products will be applied correctly and for maximum effect.

A skincare application system according to embodiments of the invention may include a package and a plurality of individually sealed applicators for applying a plurality of differing skincare products within the package, wherein each of the applicators is pre-loaded with one of the plurality of skincare products. The plurality of applicators is arranged in the package in an order that corresponds to a time-based order in which the skincare products are intended to be applied, such that removing applicators from the package in the time-based order and applying the skincare product of each removed applicator in the order that it is removed ensures application of the plurality of skincare products in a proper order according to a time-based skincare regimen. Thus, the use of the system prevents and avoids many of the problems and difficulties inherent with current skincare products. Each applicator may be pre-loaded with an effective and desired amount of the selected skincare product, thereby avoiding and reducing the chances that the user of the products will use and incorrect amount of the product, avoiding additional problems and difficulties inherent with current skincare products.

The time-based skincare regimen may be a repeating regimen that repeats once per a first time period. In such a regimen, the plurality of skincare products may include a first skincare product intended for application once at the start of a first time period and a second skincare product intended for periodic application one or more times between applications of the first skincare product. The first time period may be divisible into a plurality of intervals, such as days. The first skincare product may be intended for application at the start of the first interval, and the second skincare product may be intended for periodic application at the start of other of the plurality of intervals. For example, the second skincare product may be intended for application from two to many times as often as the first skincare product. The plurality of skincare products may include a third skincare product intended for application at the start of intervals not intended for application of either the first skincare product or the second skincare product. The frequency of application of the third skincare product may be similar to or different from the frequency of application of either the first or the second skincare products. In one example, the second and third skincare products are intended to be alternated at the start of intervals where the first skincare product is not applied. Embodiments of the system may include one or more additional skincare products to any extent desired.

In one example, the first time period is a week and the plurality of intervals are days. The first skincare product is intended for application on the first day of the week-long interval. The second and third skincare products are intended for alternating application on the second through seventh days of the week-long interval. A system and package may contain a multiple-week supply of applicators.

In one example of the skincare system, the first skincare product comprises a skincare composition comprising an effective amount of multiple alpha hydroxy acids, the second skincare product comprises a skincare composition comprising an effective amount of an antioxidant, and the third skincare product comprises a skincare composition comprising an effective amount of a retinoid. Additional details of specific compositions of representative products are disclosed in the attached Appendix.

The individually sealed applicators may be ordered in the package utilizing a variety of methods. In one example, the applicators are ordered by physical placement only, wherein each individually sealed applicator is not physically connected to any other sealed applicators, and wherein each individually sealed applicator is physically located more proximate or less proximate an opening of the package than any other individually sealed applicators. In a second example, the applicators are ordered by physical placement and connection to adjacent individually sealed applicators, wherein each individually sealed applicator is physically connected to any immediately adjacent sealed applicators, and wherein each individually sealed applicator is physically located more proximate or less proximate an opening of the package than any other individually sealed applicators. In such an example, the connection between adjacent applicators may cause the applicators to form a ribbon, string, strip, or other similar contiguous structure of individually sealed applicators. In a third example, the applicators are ordered by connection to adjacent individually sealed applicators only, wherein each individually sealed applicator is physically connected to any immediately adjacent sealed applicators as a ribbon, string, strip, or other similar contiguous structure of individually sealed applicators.

In various embodiments of the system, each of the individually sealed applicators includes a removable seal covering the skincare product preloaded on the applicator. In some instances, the seal forms a package completely enclosing the applicator. In other instances, the seal encloses only a portion of the applicator. In embodiments of the system, each of the applicators is or includes a pad configured to facilitate application of one of the skincare products. The pad may include a rear side having a sleeve configured to receive human fingers therein and a front side having an application surface preloaded at a portion thereof with one of the skincare products and a seal sealed to the application surface around the portion of the application surface preloaded with skincare product. The sleeve allows insertion of one or more of the user's fingers to facilitate application of the skincare product using the application surface. The user is able to insert one or more fingers into the sleeve, remove the seal over the skincare product, and then apply the product using the application surface as the use moves the pad over the skin using the sleeve.

In further embodiments of the invention, a skincare pad-based application system includes a package and a plurality of individually sealed pads for applying a plurality of differing skincare products within the package, wherein each of the pads is pre-loaded with one of the plurality of skincare products. The plurality of pads may be arranged in the package in an order that corresponds to a time-based order in which the skincare products are intended to be applied, such that removing pads from the package in the time-based order and applying the skincare product of each removed pad in the order that it is removed ensures application of the plurality of skincare products in a proper order according to a time-based skincare regimen. Such embodiments may include features of the embodiments discussed above wherein the "applicator" of such embodiments is a pad.

Further embodiments of the invention provide a method for producing a skincare applicator-based application system. The method includes providing a package, providing a plurality of individually sealed applicators for applying a plurality of differing skincare products, wherein each of the applicators is pre-loaded with one of the plurality of skincare products, and arranging the plurality of applicators in the package in an order that corresponds to a time-based order in which the skincare products are intended to be applied according to a time-based skincare regimen.

According to embodiments of the method, the individually sealed applicators may be ordered in the package utilizing a variety of methods. In one example, the individually sealed applicators are ordered by physical placement only, wherein each individually sealed applicator is not physically connected to any other sealed applicators, and wherein each individually sealed applicator is physically located more proximate or less proximate an opening of the package than any other individually sealed applicators. In a second example, the individually sealed applicators are ordered by physical placement and connection to adjacent individually sealed applicators, wherein each individually sealed applicator is physically connected to any immediately adjacent sealed applicators, and wherein each individually sealed applicator is physically located more proximate or less proximate an opening of the package than any other individually sealed applicators. In such an example, the connection between adjacent applicators may cause the applicators to form a ribbon, string, strip, or other similar contiguous structure of individually sealed applicators. In a third example, the individually sealed applicators are ordered by connection to adjacent individually sealed applicators only, wherein each individually sealed applicator is physically connected to any immediately adjacent sealed applicators, as a ribbon, string, strip, or other similar contiguous structure of individually sealed applicators.

In some embodiments of the method, each of the applicators includes or may be a pad configured to facilitate application of one of the skincare products. In some embodiments, the applicator includes or is a pad, and providing a plurality of individually sealed applicators for applying a plurality of differing skincare products includes loading an application surface of the pad with one of the skincare products and providing a seal over the skincare product that is sealed to the application surface around the skincare product.

Figure 1:
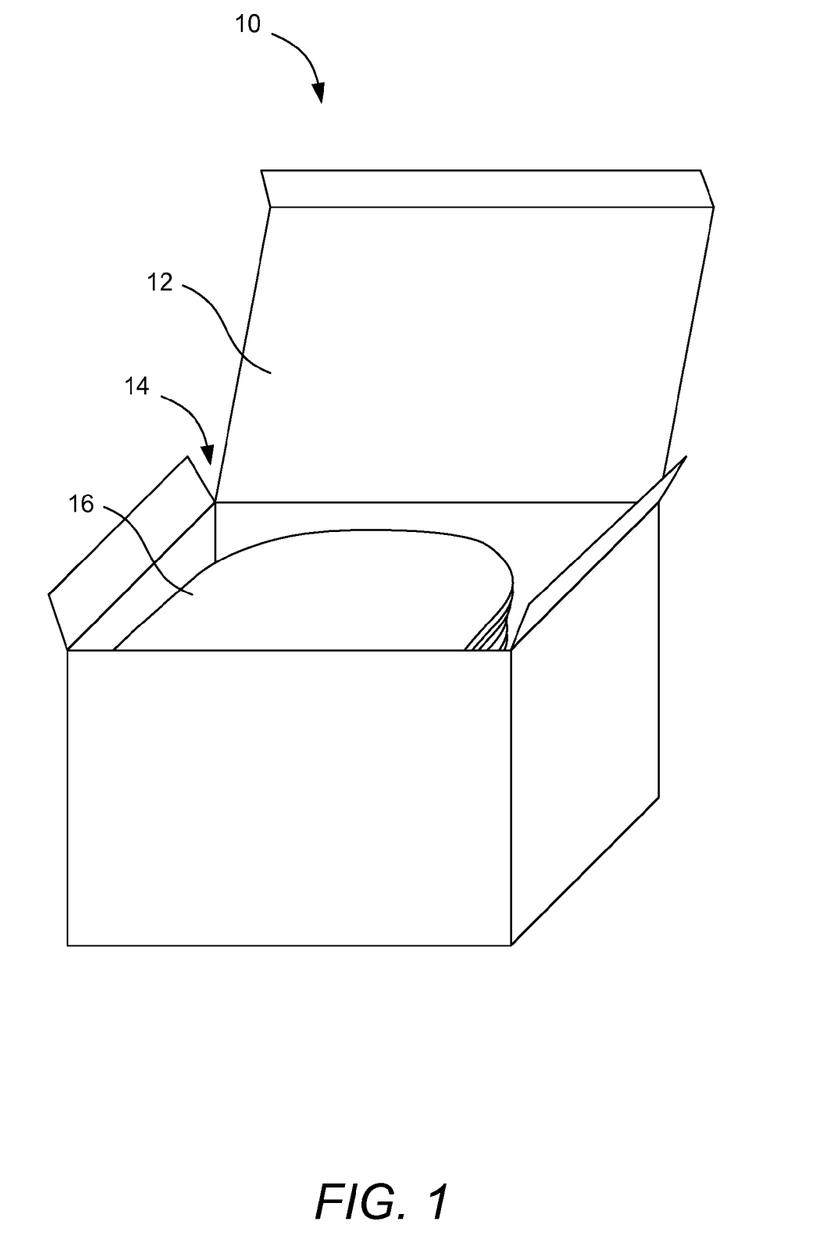
FIG. 1 shows a perspective view of a representative skincare system.

FIG. 1 shows an illustrative example of a skincare application system 10. In the illustrative system, a container containing skincare products is a box 12. The box 12 includes an opening 14. The box 12 contains individually packaged or individually sealed pads 16 that are pre-loaded with skincare products. Each of the pads 16 may contain one or a combination of skincare products designed to be applied using the pads 16, and the individual packaging or seal of each pad 16 may be opened and the product or products applied using the opened pad 16. To ensure a proper time-based order of application, the pads 16 may be arranged in the box 12 or other container or packaging in the order in which they are to be used. Thus, pads 16 to be used first are located more proximate the opening 14 of the box 12 or other container or packaging, and pads 16 to be used later are located more distal the opening 14 of the box 12 or other container or packaging. The order of the pads 16 and the proximity of the pads 16 to the opening 14 of the box 12 or other container or packaging naturally presents each pad 16 to the user in the order that pad 16 and any specific product contained thereon is to be used.

In some instances, the box 12 and/or the pads 16 may be marked with or may contain instructions for correctly ordering the pads 16 in the box 12 in the event the pads 16 become disordered. The pads 16 may also include special markings or colorings on the pads 16 themselves or on packaging or seals of the pads 16 to facilitate reordering. If, for example, the box 12 or other container or packaging is dropped and the contents are spilled out, the original ordering of the pads 16 may be lost. Similarly, the box 12 or other container or packaging may be inadvertently tipped over and the original ordering similarly lost. In such a circumstance, the user would still be able to restore the original order by following the instructions to reorder the pads 16 in the box 12 or other container or packaging. This restoration of the order is a one-time process, and the system 10 would be restored to a state in which the user need not think about the order of application of the skincare products, but could simply return to using the uppermost pad 16 in the box 12 or other container or packaging.

In one example of a skincare regimen, for example, a twenty-eight day regimen of products to be applied one product per day might be arranged in the box 12 or other container or packaging in an order of intended application. The regimen may include three products, product A (e.g. a skincare product intended to peel and brighten skin), product B (e.g. a skincare product designed to soothe and protect/shelter skin), and product C (e.g. a skincare product intended to lift/uplift and firm). Product A may be intended for application once per week, with products B and C intended for application every other day on days when product A is not applied.

Thus, the pads 16 may be arranged inside the box 12 or other container or packaging in the following order (from top to bottom or most proximal to the opening 12 to most distal from the opening): A, B, C, B, C, B, C, A, B, C, B, C, B, C, A, B, C, B, C, A, B, C, B, C, B, C. Each day, the user removes the uppermost pad 16 from the box 12, opens the pad's packaging and/or seal, and applies the product using the pad 16 according to application instructions (e.g. either on or in the box 12, on the packaging and/or seal for the individual pad 16, or printed on the pad 16 itself).

As may be appreciated, if the user simply had bottles of product, the user might have a difficult time remembering on which day in the skincare regimen the user was on, and might therefore apply an incorrect product. The incorrect application of products could lessen the effectiveness of the skincare regimen, or could even lead to temporary or permanent skin damage. The skincare system 10 using individually sealed pads 16 ordered in the box 12 or other container or packaging to present the pads 16 to the user in the correct order obviates such problems.

A skincare regimen such as that described above may be advantageous in conjunction with a variety of differing skincare products that are intended for application in a time-based fashion. For example, a skincare product intended to peel and brighten skin may provide exfoliation and results similar to a microdermabrasion treatment. Such a treatment, however, may be inappropriate for daily use, for example, and may instead be better suited for once-weekly use. Arrangement of pads 16 containing skincare products in the box 12 so as to cause pads 16 containing the skincare product intended to peel and brighten skin to be the uppermost pad 16 only once a week will reduce the chances that the user will inadvertently over-apply such a more-aggressive skincare product. As an example of the skincare product intended to peel and brighten skin, such a product may include effective amounts of multiple alpha hydroxy acids as ingredients, such as lactic acid, salicylic acid, and/or glycolic acid. As a more specific example, the peel and brighten skincare product may comprise approximately 5% of each alpha hydroxy acid, such as 5% lactic acid, 5% salicylic acid, and 5% glycolic acid. Other effective amounts of one or more alpha hydroxy acids may be used, and the effect of such skincare products is to dissolve away and remove the surface layer of dead skin cells.

As discussed above, on days when the skincare product intended to peel and brighten skin is not to be used, skincare products intended to soothe and protect/shelter the skin and skincare products intended to lift/uplift and firm skin may be alternated. The alternation is achieved by alternating an appropriate number of pads 16 containing the respective soothe and protect/shelter and lift/uplift and firm skincare products in the box 12 or other container or packaging between the pads 16 containing the skincare product intended to peel and brighten the skin. A skincare product intended to soothe and protect/shelter the skin may include an effective amount of a variety of antioxidants as ingredient(s) for purposes of fighting free radicals and environmental damage and for soothing the skin. One example of an antioxidant is epigallocatechin gallate (EGCG), commonly found in green tea (camellia sinensis) and green tea leaf extract. A skincare product intended to soothe and protect/shelter the skin may include an effective amount of EGCG or any other desired antioxidant.

A skincare product intended to lift/uplift and firm skin may include an effective amount of a retinoid solution as an ingredient for purposes of stimulating collagen production. One example of a retinoid that may be used in the lift/uplift and firm product is retinol. Other retinoids may be substituted as needed. The materials included in the Appendix give more details of specific examples of skincare products that may be included on the pads 16 and the compositions and ingredients thereof, as well as a specific example of the ordering of the pads 16 into a multi-week skincare regimen. Nevertheless, the specific examples contained and discussed in the Appendix are intended to be exemplary only, and are not intended to be limiting.

For example, the specific examples of the Appendix discuss a package containing a four-week supply of three different skincare products on pads 16 arranged in a repeating weekly schedule of products, one product per day. Embodiments of the invention embrace skincare regimens that repeat on a different schedule, intervals of application that are longer or shorter than one day, a number of skincare products in the regimen that varies between two skincare products and as many as desired, and packaging more or fewer pads 16 in the outer container or other packaging than the amount disclosed and discussed in the Appendix.

A time-based arrangement of products in a container, box 12, or other packaging as described above and in the attached Appendix is only one example of a way in which a time-based regimen of various products may be packaged and sold. As another example, the pads 16 or some other applicator may be individually packaged or sealed in a ribbon, string, strip, or other contiguous structure of packaging such that an individual pad 16 or other applicator can be torn, separated, or otherwise removed from one end of the ribbon, string, strip, or other contiguous structure and used, and the next day the next pad 16 or other applicator in the ribbon, string, strip or other contiguous structure can be used in similar fashion. In some instances, such arrangement of pads 16 or other applicators in the ribbon, string, strip or other contiguous structure may be combined with packaging in an outer package or container such as the box 12, as illustrated in FIGS. 2 and 3.

Figure 2:
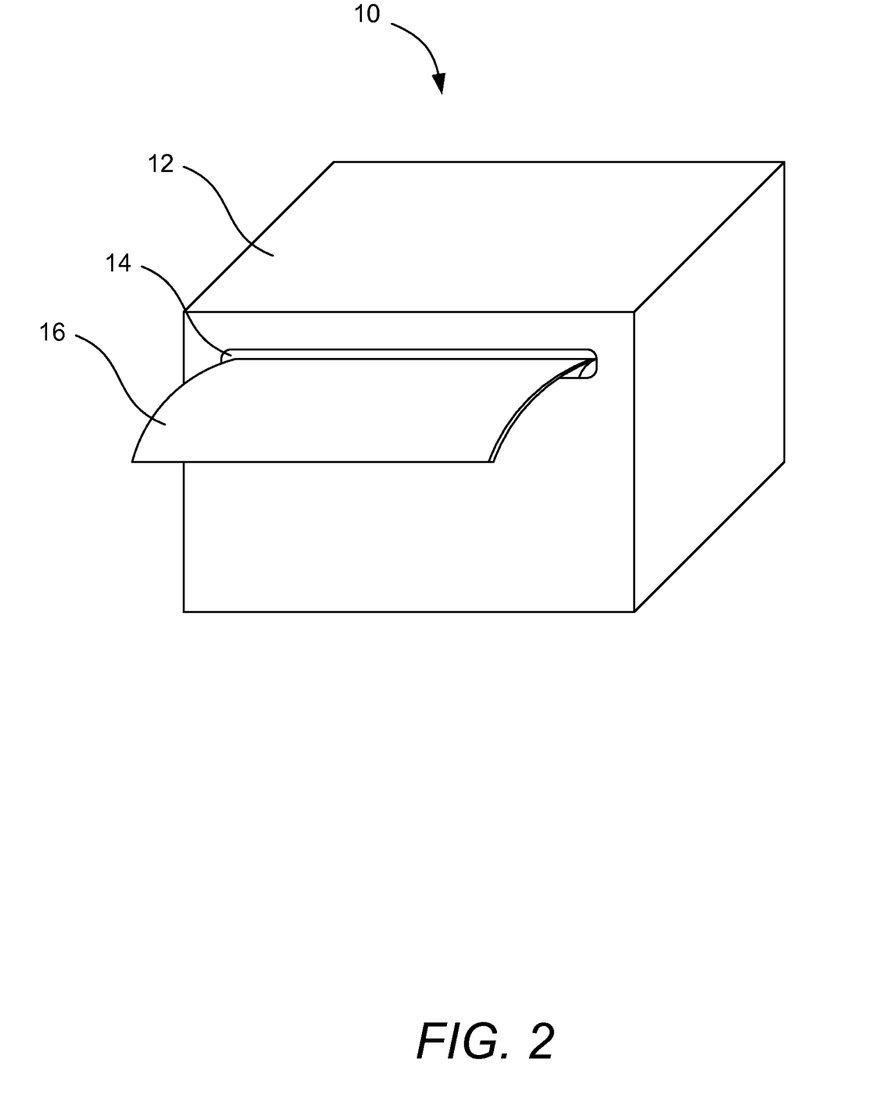
FIG. 2 shows a perspective view of an alternate skincare system.

FIG. 2 shows an alternate embodiment of the skincare application system 10. This embodiment also includes a box 12 or other container or packaging. The box 12 or other container or packaging also contains an opening 14. The box 12 or other container or packaging also contains pads 16 or other applicators pre-loaded with varying skincare products and ordered to present the proper skincare products to the user in a proper order. In this embodiment, however, the pads 16 or other applicators are disposed in the box 12 or other container or packaging connected to one another in any appropriate manner as a single contiguous ribbon, string, strip, or other contiguous structure, rather than simply individually stacked as in the example of FIG. 1.

The continuous ribbon, string, strip, or other contiguous structure may be contained in the box 12 or other container or packaging in any appropriate manner. As one example, the continuous ribbon, string, strip, or other contiguous structure may be rolled up inside the box 12 or other container or packaging, such as is illustrated in FIG. 2. In such an instance, as may be appreciated, as the pads 16 are unrolled from the roll, they may vary in proximity to the opening 14, but the correct pad 16 will always be presented to the user at the appropriate time.

Figure 3:
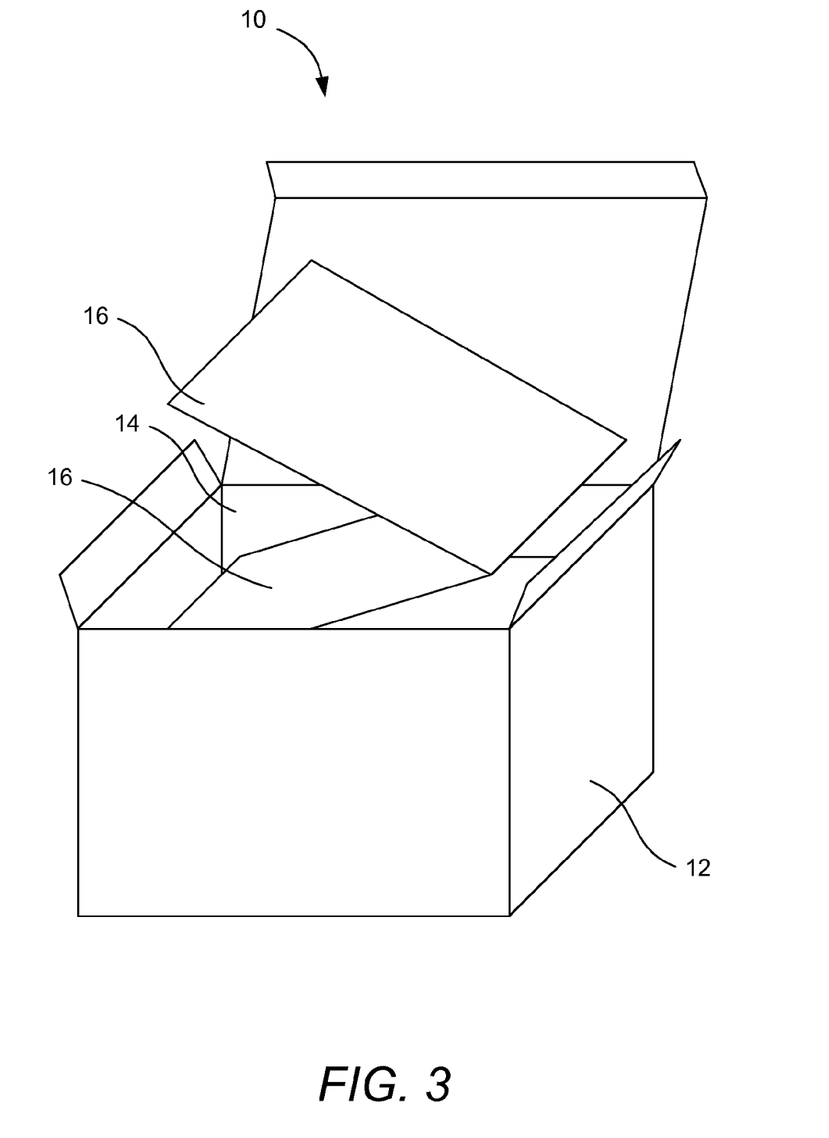
FIG. 3 shows a perspective view of an alternate skincare system.

As another example, the continuous ribbon, string, strip, or other contiguous structure may be folded back and forth inside the box 12 or other container or packaging, such as is illustrated in FIG. 3. In this example, the ordering of pads still maintains the order of pads to be used by proximity to the opening 14 in a fashion similar to that discussed above with respect to FIG. 1. In either example of FIG. 2 or FIG. 3, the contiguous nature of the continuous ribbon, string, strip, or other contiguous structure assists in maintaining the proper order of the pads 14 or other applicators. In the event the structure falls from the box 12 or other container or packaging, the continuous ribbon, string, strip, or other contiguous structure is simply returned to the box 12 or other container or packaging, with care in the case of the example of FIG. 3 to ensure that the continuous ribbon, string, strip, or other contiguous structure is properly oriented up or down. The last pad 16 or other applicator or packaging thereof of the continuous ribbon, string, strip, or other contiguous structure may be marked with an appropriate designation to assist in proper orientation, such as the designation "Use this pad last," or "This pad should be at the bottom of the box."

Regardless of the manner in which the continuous ribbon, string, strip, or other contiguous structure is disposed in the box 12, container, or other packaging, the user accesses the next pad 16 or other applicator to be used by pulling it (or its associated individual packaging containing the pad 16 or other applicator) through the opening 14 in the box 12 or other container or packaging, and by separating it from the remaining continuous ribbon, string, strip, or other contiguous structure. The next pad 16 or other applicator is thereby disposed most proximate the opening 14 or is otherwise most easily accessible and ready for use at the next time a pad 16 or other applicator is to be used.

Figure 4:
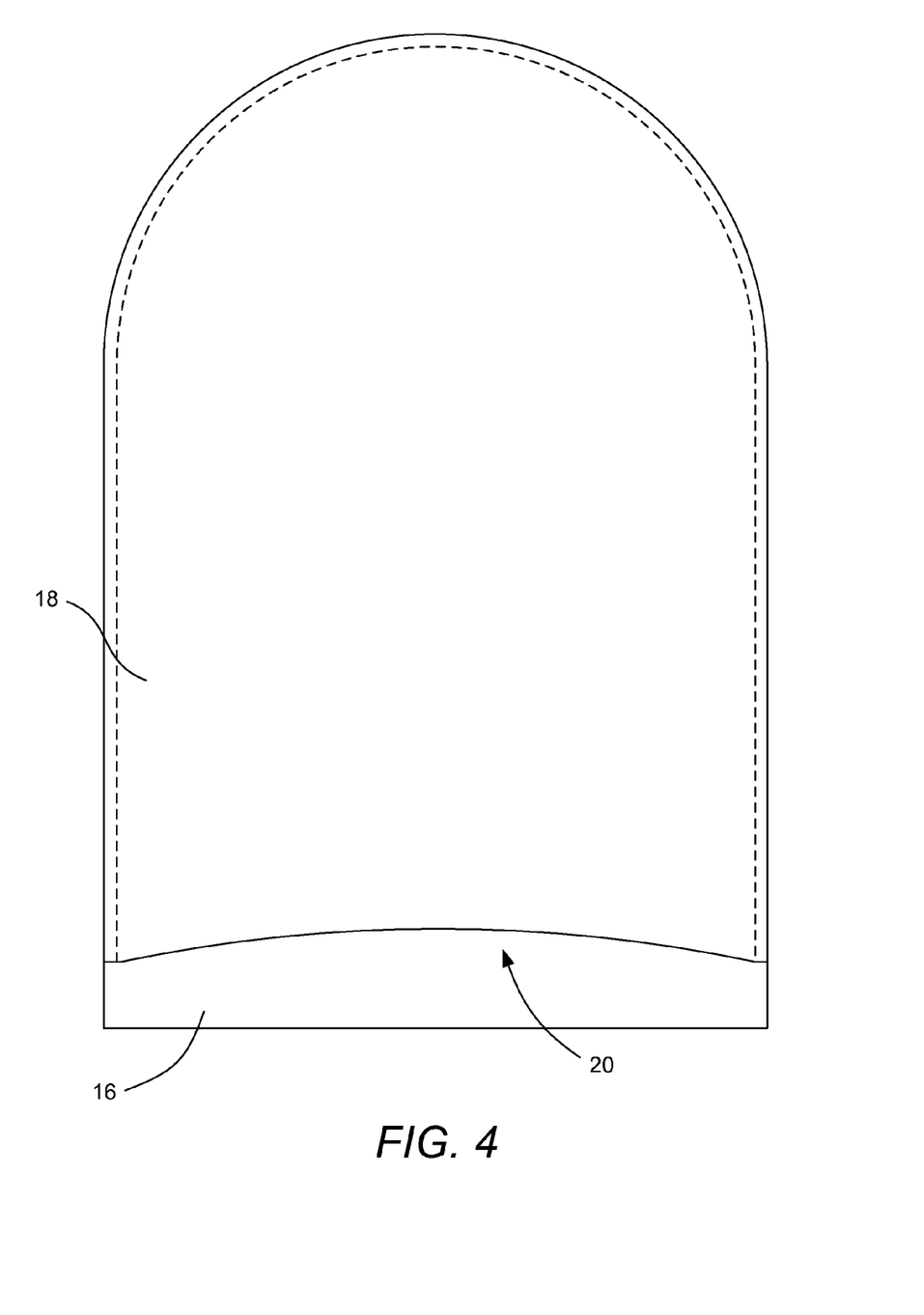
FIG. 4 shows a plan view of a rear surface of a representative pad from a skincare system.
Figure 5:
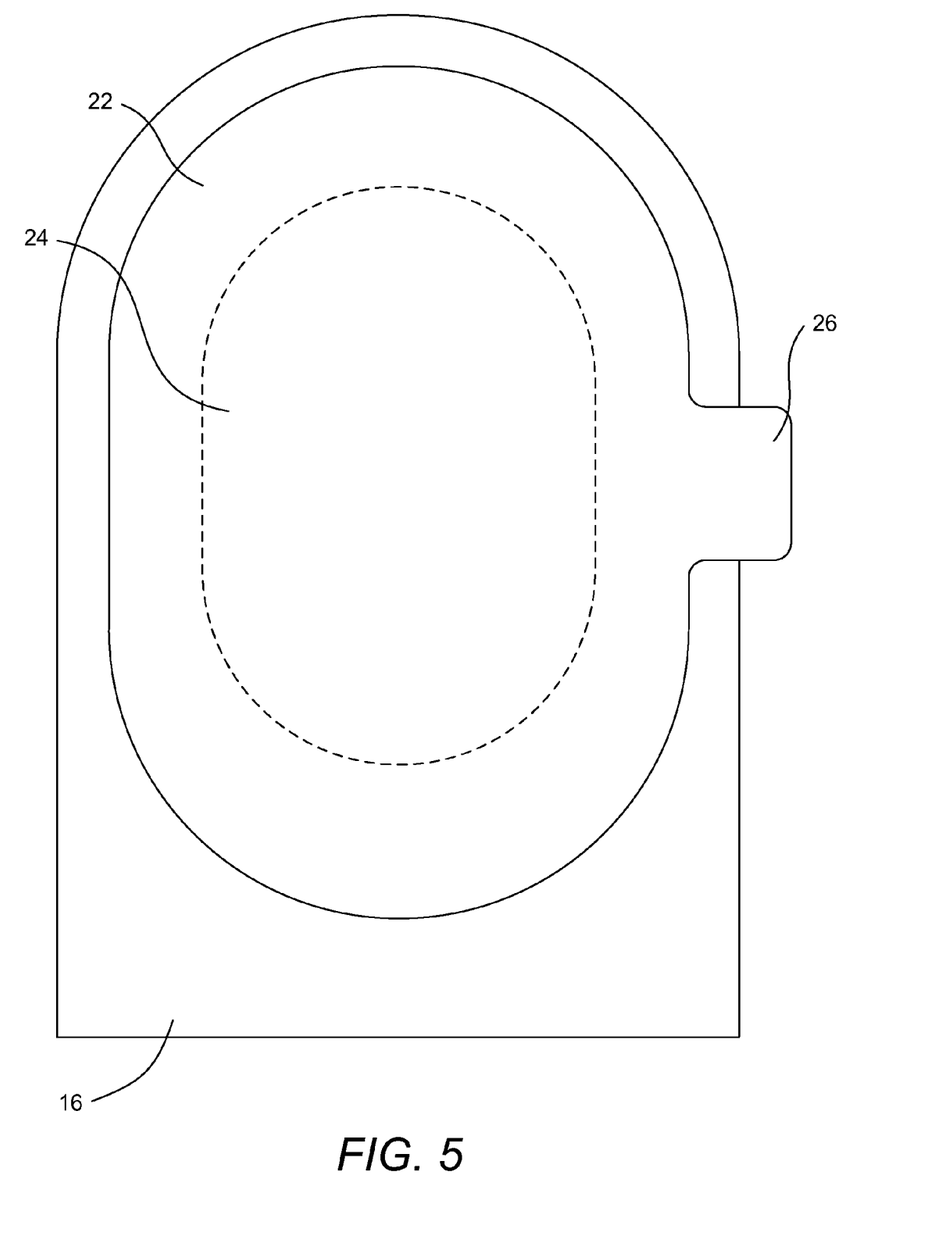
FIG. 5 shows a plan view of a front surface of the representative pad of FIG. 4.

While the pads 16 or other applicators may take any desirable functional or aesthetic shape, FIGS. 4 and 5 present back and front plan views of an illustrative pad 16, similar in shape to the pads 16 shown in FIG. 1. FIG. 4 shows a back plan view of the pad 16, and shows that the pad 16 includes a sleeve 18 that forms an opening 20 configured to receive one or more fingers of the user therein. The user is able to insert one or more fingers into the sleeve to hold, control, and manipulate the pad 16, such as by drawing and maneuvering the pad 16 across the skin to apply the skincare product.

FIG. 5 shows a front plan view of the pad 16. The front side of the pad 16 includes or forms an application surface configured to facilitate application of the skincare product, as is known in the skincare and skincare pad/applicator art. A portion of the application surface is covered by a seal 22 that covers and seals in an effective amount of a skincare product 24. The seal 24 is sealed to the application surface around the skincare product 24, keeping the skincare product therein. Underneath the skincare product 24, the pad 16 includes one or more layers that prevent leakage of the skincare product backward through the pad 16. The seal 22 includes a tab 26 or other structure that is not sealed to the application surface, to facilitate removal of the seal 22.

In use, the user inserts one or more fingers into the opening 20 of the sleeve 18. The user then grasps the tab 26 or other structure of the seal 22 and removes the seal 22 from the pad 16. This exposes the skincare product. The user then manipulates the pad 16 over the skin with the application surface directed toward the skin, applying the skincare product to the skin.

The attached materials of the Appendix are incorporated into this disclosure in their entirety, as if set forth in full herein. In the claims, the term "ribbon" is intended to embrace an contiguous structure of individual separable components, including ribbons, strings, strips, and the like.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A skincare application system comprising:
    a package;
    a plurality of individually sealed applicators within the package, each of the individually sealed applicators being pre-loaded with and adapted for applying one of a plurality of differing skincare products;
    wherein the plurality of applicators is arranged in the package in an order that corresponds to a time-based order in which the skincare products are intended to be applied, such that removing applicators from the package in the time-based order and applying the skincare product of each removed applicator in the order that it is removed ensures application of the plurality of skincare products in a proper order according to a time-based skincare regimen;
    wherein the time-based skincare regimen comprises a repeating regimen that repeats once per week, and wherein the plurality of skincare products comprises:
        a first skincare product intended for application once on a first day of a week;
        a second skincare product and a third skincare product intended for alternating application, one skincare product per day, on the second through seventh days of the week.

2. A system as recited in claim 1, wherein:
    the first skincare product comprises a skincare composition comprising an effective amount of multiple alpha hydroxy acids;
    the second skincare product comprises a skincare composition comprising an effective amount of an antioxidant; and
    the third skincare product comprises a skincare composition comprising an effective amount of a retinoid.

3. A system as recited in claim 1, wherein the package contains a multiple-week suply of applicators.

4. A skincare application system as recited in claim 1, wherein the package defines a unitary volume contained thereby.

5. A system as recited in claim 1, wherein:
the first skincare product comprises a product to exfoliate and brighten skin;
the second skincare product comprises a product to fight free radicals and soothe and protect skin; and
the third skincare product comprises a product to stimulate collagen production in skin.

6. A system as recited in claim 1, wherein the individually sealed applicators are ordered in the package utilizing a method selected from the group consisting of:
physical placement only, wherein each individually sealed applicator is not physically connected to any other sealed applicators, and wherein each individually sealed applicator is physically located more proximate or less proximate an opening of the package than any other individually sealed applicators;
physical placement and connection to adjacent individually sealed applicators, wherein each individually sealed applicator is physically connected to any immediately adjacent sealed applicators, and wherein each individually sealed applicator is physically located more proximate or less proximate an opening of the package than any other individually sealed applicators; and
connection to adjacent individually sealed applicators only, wherein each individually sealed applicator is physically connected to any immediately adjacent sealed applicators as a ribbon of individually sealed applicators.

7. A system as recited in claim 1, wherein each of the individually sealed applicators comprises a removable seal covering the skincare product preloaded on the applicator.

8. A system as recited in claim 1, wherein each of the applicators comprises a pad configured to facilitate application of one of the skincare products.

9. A system as recited in claim 8, wherein the pad comprises:
a rear side comprising a sleeve configured to receive human fingers therein; and
a front side comprising:
an application surface preloaded at a portion thereof with one of the skincare products; and
a seal sealed to the application surface around the portion of the application surface preloaded with skincare product.

10. A skincare application system as recited in claim 1, wherein the system is pad-based and wherein the package comprises a box; and
wherein the plurality of applicators are a plurality of individually sealed pads contained within the box.

\* \* \* \* \*